United States Patent
Imwinkelried et al.

(10) Patent No.: US 10,039,580 B2
(45) Date of Patent: Aug. 7, 2018

(54) CONTROLLING THE DEGRADATION OF BIORESORBABLE METAL IMPLANTS

(75) Inventors: Thomas Imwinkelried, Seltisberg (CH); Elliott Gruskin, Malvern, PA (US); Andrea Montali, Basel (CH); Stefan Beck, Niederdorf (CH)

(73) Assignee: Depuy Synthes Products, Inc., Raynham, MA (US)

( * ) Notice: Subject to any disclaimer, the term of this patent is extended or adjusted under 35 U.S.C. 154(b) by 819 days.

(21) Appl. No.: 13/213,213

(22) Filed: Aug. 19, 2011

(65) Prior Publication Data

US 2012/0053637 A1     Mar. 1, 2012

Related U.S. Application Data

(60) Provisional application No. 61/378,747, filed on Aug. 31, 2010.

(51) Int. Cl.
*A61B 17/80* (2006.01)
*A61B 17/86* (2006.01)

(52) U.S. Cl.
CPC ............ *A61B 17/80* (2013.01); *A61B 17/866* (2013.01)

(58) Field of Classification Search
USPC .................. 606/280, 286, 298, 291, 293
See application file for complete search history.

(56) References Cited

U.S. PATENT DOCUMENTS

| | | | |
|---|---|---|---|
| 4,530,115 A * | 7/1985 | Muller et al. | 623/23.18 |
| 6,022,350 A | 2/2000 | Ganem | |
| 6,673,469 B2 * | 1/2004 | Isacsson et al. | 428/642 |
| 7,104,991 B2 * | 9/2006 | Dixon et al. | 606/279 |
| 7,674,279 B2 | 3/2010 | Johnson | |
| 2002/0103488 A1 | 8/2002 | Lower et al. | |
| 2002/0151898 A1 | 10/2002 | Sohngen et al. | |
| 2004/0006345 A1 | 1/2004 | Vlahos et al. | |
| 2005/0010225 A1 * | 1/2005 | Del Medico | 606/69 |
| 2005/0075633 A1 | 4/2005 | Ross | |
| 2005/0187552 A1 | 8/2005 | Michelson | |
| 2006/0229711 A1 | 10/2006 | Yan et al. | |
| 2007/0213728 A1 | 9/2007 | Lindemann | |
| 2007/0288016 A1 | 12/2007 | Halder | |
| 2008/0091206 A1 | 4/2008 | Johnson | |
| 2008/0200955 A1 * | 8/2008 | Tepic | 606/289 |

(Continued)

FOREIGN PATENT DOCUMENTS

| | | |
|---|---|---|
| CN | 101257860 A | 9/2008 |
| CN | 101283922 A | 10/2008 |

(Continued)

OTHER PUBLICATIONS

Shi, D.; Introduction to Biomaterials; 2006; Tsinghua University Press; p. 136.*

(Continued)

*Primary Examiner* — Nicholas Woodall
(74) *Attorney, Agent, or Firm* — Baker & Hostetler LLP

(57) ABSTRACT

A degradation controlled metal implant and methods of controlling the degradation of the implant. In one embodiment, the implant includes a body, one or more apertures, and one or more fastener blanks fixed within one or more apertures. In another embodiment, the implant includes a body of a first material and a second material plated in various patterns over the first material.

13 Claims, 3 Drawing Sheets

(56) References Cited

U.S. PATENT DOCUMENTS

| | | | |
|---|---|---|---|
| 2009/0118770 A1* | 5/2009 | Sixto et al. | 606/280 |
| 2009/0198286 A1* | 8/2009 | Lozier et al. | 606/298 |
| 2009/0264924 A1 | 10/2009 | Ushiba | |
| 2011/0087229 A1* | 4/2011 | Kubiak et al. | 606/70 |

FOREIGN PATENT DOCUMENTS

| | | |
|---|---|---|
| CN | 101415374 | 4/2009 |
| CN | 101621966 | 1/2010 |
| EP | 0682917 | 11/1995 |
| JP | 2008-114076 | 5/2008 |
| WO | WO 2006/108065 | 10/2006 |
| WO | WO 2007/082004 | 7/2007 |
| WO | 2009155715 | 12/2009 |

OTHER PUBLICATIONS

International Search Report and Written Opinion for PCT/2011/048362 dated Jun. 11, 2012.

\* cited by examiner

CONTROLLING THE DEGRADATION OF BIORESORBABLE METAL IMPLANTS

CROSS-REFERENCE TO RELATED APPLICATION

This application claims the benefit of U.S. Provisional Application No. 61/378,747, filed Aug. 31, 2010, which is incorporated herein by reference in its entirety.

BACKGROUND OF THE INVENTION

The present invention relates to a degradation controlled metal implant and methods of controlling the degradation of the implant.

In the case of metals, the most destructive type of degradation results from electrochemical or galvanic attack, often thought of as being chemical in nature. The terms "degradation" and "corrosion" are used interchangeably herein.

The use of degradable implant material is known in the art. However, due to certain factors, including metal type and surface-to-volume ratio, certain implants either degrade too fast or degrade too slow. The present invention addresses this problem.

BRIEF SUMMARY OF THE INVENTION

The present invention relates to a degradation controlled metal implant and methods of controlling the degradation of the implant.

In at least one aspect, the present invention is directed towards an implant secured to tissue that includes a body including a first material and a plurality of apertures; a fastener disposed within at least one of the plurality of apertures and secured to the tissues; and a fastener blank disposed within at least one aperture, the blank being configured to substantially fill the aperture in which it is disposed without substantially protruding from the body.

In one embodiment, the fastener blank includes a screw head securely locked to the body.

In another embodiment, the fastener blank includes a second material that is less noble than the first material.

In another embodiment, the fastener blank comprises a second material that is more noble than the first material.

In at least one aspect, the present invention is directed towards a tissue implant that includes a body configured to be implanted in tissue, the body comprising a first metallic material and a second metallic material, the first metallic material being more noble than the second metallic material.

In one embodiment, the body includes a cannulated fastener including the first metallic material, the cannulated fastener having a cannula, and a wire insert including the second material, the wire configured to closely fit within the cannula.

In another embodiment, a majority of the body is configured from the first metallic material and the second metallic material is welded or plated to the first metallic material.

In another embodiment, the body includes a plate having a plurality of apertures substantially surrounded by the first material and a prolongation substantially including the second material.

In another embodiment, the second material comprises an alloy of the first material.

In another embodiment, a majority of the body consists essentially of the first material and a minority of the body consists essentially of the second material.

In another embodiment, the minority of the body reflects as one or more discrete segments on a surface of the tissue implant.

In another embodiment, the one or more discrete segments include a line, a dot, a logo, a regular geometric pattern, an irregular geometric pattern or combinations thereof.

In at least one aspect, the present invention is directed towards a method of controlling the degradation of a tissue implant including providing an implant having at least one aperture, the implant having a body consisting essentially of a first material; securing the implant to tissue; and positioning an insert within the aperture to substantially fill the aperture, the insert consisting essentially of a second material that is of a lower nobility than the first material.

In at least one aspect, the present invention is directed towards a method of controlling the degradation of a tissue implant including providing a first implant having a plurality of apertures and at least one fastener blank; inserting fasteners through some but not all of the apertures to secure the plate to the bone; and after securing the plate to the bone, permitting the at least one fastener blank to be inserted in at least one of the plurality of apertures that do not contain an inserted fastener.

BRIEF DESCRIPTION OF THE SEVERAL VIEWS OF THE DRAWINGS

The foregoing summary, as well as the following detailed description of embodiments of the present invention, will be better understood when read in conjunction with the appended drawings of exemplary embodiments. It should be understood, however, that the invention is not limited to the precise arrangements and instrumentalities shown.

In the drawings.

DETAILED DESCRIPTION OF THE INVENTION

With reference to the accompanying drawings, various embodiments of the present invention are described more fully below. Some but not all embodiments of the present invention are shown. Indeed, various embodiments of the invention may be embodied in many different forms and should not be construed as limited to the embodiments expressly described. Like numbers refer to like elements throughout. The singular forms "a," "an," and "the" include the singular and plural unless the context clearly dictates otherwise.

Figure 1:
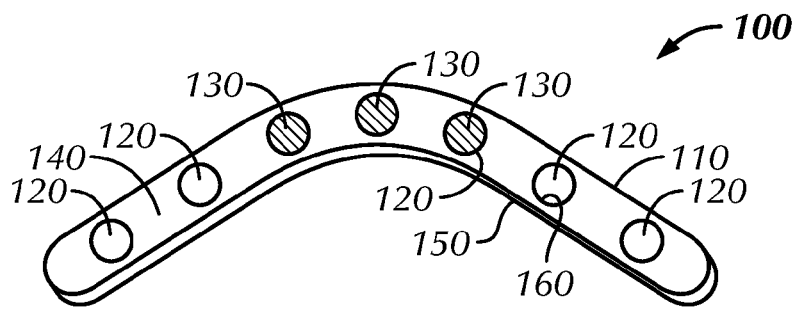
FIG. 1 illustrates an exemplary top view of a tissue implant according to one embodiment of the present invention.

As shown generally in FIG. 1, embodiments of the present invention are directed toward a tissue implant 100. In some embodiments, tissue implant 100 includes a body 110 and one or more apertures 120. In one embodiment, struts 140 surround or immediately abut apertures 120.

Figure 2:
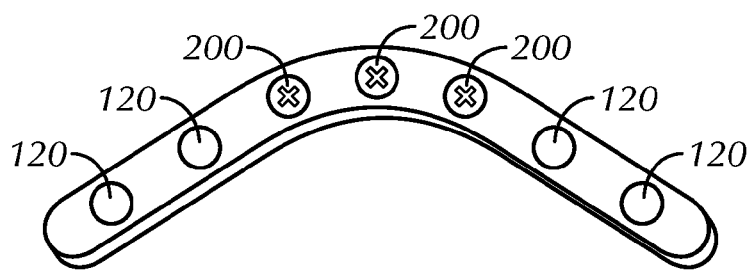
FIG. 2 illustrates an exemplary top view of a tissue implant according to one embodiment of the present invention.
Figure 3:
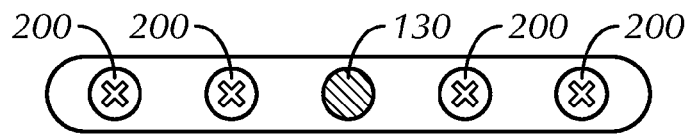
FIG. 3 illustrates an exemplary top view of a tissue implant according to one embodiment of the present invention.
Figure 4:
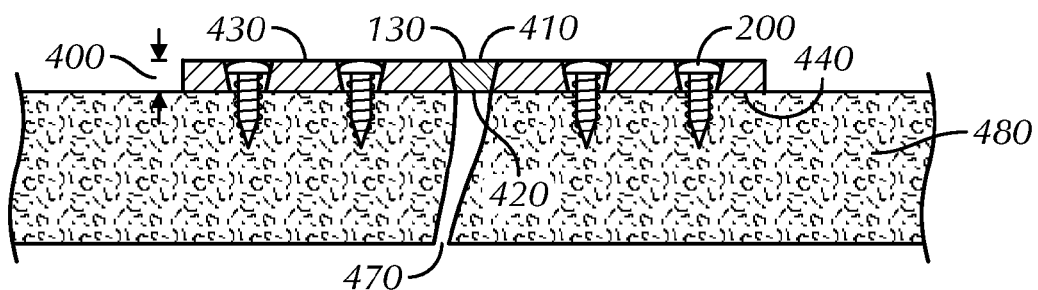
FIG. 4 illustrates an exemplary cross-sectional view of the tissue implant of FIG. 3 fastened to a tissue (e.g., bone) according to one embodiment of the present invention.
Figure 5:
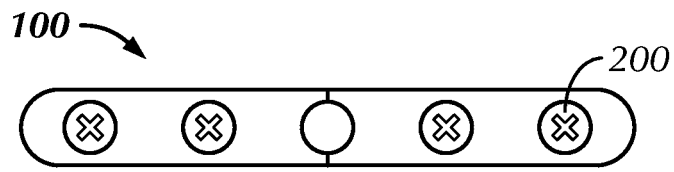
FIG. 5 illustrates an exemplary top view of a tissue implant according to one embodiment of the present invention.

As illustrated in FIGS. 1-7, implant 100 may include a thickness 400 such as the thickness of the plate illustrated in FIG. 4. Implant 100 may include a linearly configured plate (e.g., as illustrated in FIG. 3) or a plate in an angular configuration (e.g., as illustrated in FIGS. 1 and 2). Implant 100 is not limited however to a plate and may include any other tissue implant. Implant 100 may further include one or more fasteners 200. Fasteners 200 may include threaded fasteners (e.g., screws, cannulated screws); and non-threaded fasteners (e.g., wires, K-wires, cannulas).

In one embodiment, implant 100 includes fastener blank 130. Fastener blank 130 may include a screw blank (e.g., a blind screw) or a bolt blank (e.g., a blind bolt). In one embodiment, a screw blank or bolt bank is a screw or bolt with a head that can be threaded for a specific application. In one embodiment, fastener blank 130 comprises a head with no shank. In one embodiment, fastener blank 130 has a uniform diameter throughout its length. In one such application the screw head or bolt head is threaded to match threads in apertures 120. In one embodiment, fastener blank 130 includes a head that is configured to snap fit within apertures 120. In another embodiment, fastener blank 130 includes a head configured to press fit within aperture 120. In one embodiment, fastener blank 130 is configured to securely lock to body 110.

In one embodiment, fastener blanks 130 (e.g., blind screws) are used to protect locking threads during bending (e.g., pre-bending) of an implant such as a plate. After the bending operation, the fastener blank 130 may be removed and later replaced with fasteners such as a screw, bolt, or threaded wire. In other embodiments, the fastener blank 130 may be left in place after bending to be implanted as described herein. In one such embodiment, the degradation rate of struts 140 is reduced or substantially eliminated where implanted fastener blanks are included in an implanted implant 100. In one embodiment, degradation is retarded more from either the top or bottom of implant 100 when a fastener blank 130 is implanted within an aperture with implant 100. In one embodiment, degradation of implant 100 occurs only from an outside face 150 of implant 100.

Figure 12:
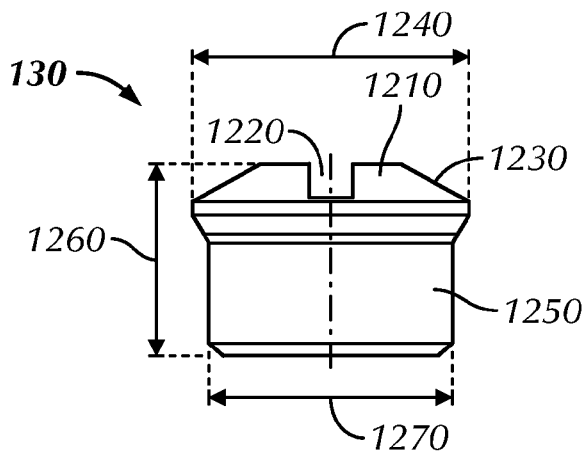
FIG. 12 illustrates an exemplary cross-section view of a fastener blank according to one embodiment of the present invention.
Figure 13:
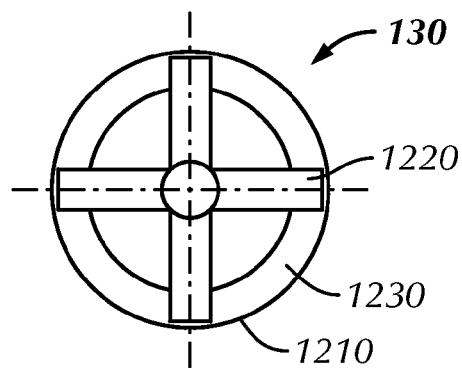
FIG. 13 illustrates an exemplary top view of a fastener blank according to one embodiment of the present invention.

One example of fastener blank 130 is illustrated in FIGS. 12 and 13. In one embodiment, fastener blank 130 has a predetermined height 1260, a substantially saucer-shaped head 1210 and a body 1250. In one embodiment, the head 1210 has a cross-shaped grove 1220 formed thereon so as to engage with the distal engaging portion of a rotary fastening tool or a driver bit (not shown). In another embodiment, said head 1210 has a predetermined width 1240. In one embodiment, said head 1210 has a tapered side peripheral portion 1230.

Fastener blank 130 as illustrated in FIGS. 12 and 13 also includes a body 1250 extending downward from the head 1210. In one embodiment, said body has a predetermined width 1270. In one embodiment, the tapered portion 1230 is linearly tapered off. In one embodiment (not illustrated), width 1240 of fastener blank 130 is substantially equal to width 1270 of fastener blank 130. Fastener blank 130 may be threaded across all or a portion of height 1260.

Fastener blank 130 may be configured and dimensioned to extend a predetermined length within aperture 120. In one embodiment, fastener blank 130 is configured to substantially fill aperture 120. In one embodiment, fastener blank 130 substantially or completely fills aperture 120 but does not protrude from body 110 or implant 100. For example, as illustrated in FIG. 4, fastener blank 130 has a first end 410 and a second end 420 that are coterminous with a first face 430 and second face 440 of implant 100. In one embodiment, fastener blank 130 has a length that is substantially equivalent to thickness 400.

In one embodiment, illustrated in FIG. 4, implant 100 is secured to tissue 480 (e.g., bone) with one or more fasteners 200. In one embodiment a fastener is disposed within at least one of a plurality of apertures of body 120 and is secured to tissue 480. In one embodiment, a fastener blank 130 is disposed within at least one aperture 120 (e.g., one of the apertures 120 that is not receiving a fastener 200). As illustrated in FIG. 1, more than one fastener blank 130 is disposed within implant 100. As illustrated in FIG. 4, implant 100 includes four fasteners 200 and one fastener blank 130. In one embodiment, fastener blank 130 is configured to align with a fracture 470 within tissue 480. To achieve the beneficial affect described herein, a fastener blank 130 can be applied in any other position of a plate where the biomechanical situation allows for it.

In some embodiments, implant 100 comprises a material that is degradable (e.g., a degradable metal or polymer). Degradable metals that are useful in the present invention include magnesium and degradable iron and their alloys. In one embodiment, implant 100 comprises at least two different materials (e.g., two different metals having a different electrode potential or electrochemical potential. Magnesium, for example, has a standard electrode potential of −2.37 V; Iron has a standard electrode potential of of −0.44 V.). For example, in one embodiment, body 110 may comprise or substantially consist of a material having a first nobility and a fastener blank 130 comprising or consisting essentially of a second material having a nobility that is different from the first material. In one embodiment, the first material is more noble than the second material. In another embodiment, the second material is more noble than the first embodiment. In one embodiment, the second material is an alloy of the first material. In a further embodiment, the second material is not an alloy of the first material.

Thus, for example, implant 100 may include a plate having a body 110 consisting essentially of magnesium and a fastener blank 130 consisting essentially of a magnesium alloy. Such alloys may include Yttrium and/or rare earth containing alloys such as WE43 or WE54. In one embodiment, implant 100 comprises two metals that are both alloys.

Alternatively, implant 100 may include a plate having a body 110 consisting essentially of magnesium, iron or alloys thereof and a fastener blank consisting essentially of a more noble metal such as gold or silver. In one embodiment, the presence of the more noble metal permits the degradation of body 110 faster than it would degrade without the more noble material.

Thus, embodiments of the present invention may provide several advantages. For example, in one embodiment, implant 100 may be implanted with a degradation characteristic that is controlled based upon the materials selected and the designed features of the implant. For example, whereas a prior art magnesium implant 100 implanted for the purpose, for example, of reducing a fracture, is a bone plate. The plate may include apertures 120 that accommodate bone screws fixing the plate to bone. Prior to the present invention, plate apertures 120 may have been left open in proximity of the fracture. In that instance, plate degradation might occur from both sides of plate aperture 120 and may be hastened from the interior of the plate. In one embodiment of the present invention, fastener blanks fixed within otherwise open apertures 120 may retard or substantially eliminate that degradation. Alternatively, fastener blanks comprising material that is more degradable than the material making up body 110 may be implanted. In such case, the more degradable fastener blank may be sacrificially degraded in order to further retard the degradation of body 110.

The control of degradation disclosed herein is not limited to implants having fastener blanks. For example, in one embodiment there is a tissue implant 100 (e.g., as illustrated FIGS. 6 and 7) having a body 110 that comprises a first material portion 610 and a second material portion 620.

In one embodiment, first material portion 610 may comprise or consist essentially of a first material and the second material portion 620 may comprise or consist essentially of a second material. In one embodiment such first material may degrade when exposed to bodily fluids at a rate that is different than the degradation rate of the second material. In one embodiment, the second material portion 620 may be configured as a sacrificial anode relative to the first material portion 610. In one embodiment, second material portion 620 may comprise or consist essentially of a less noble metal alloy than that of first material portion 610. In one embodiment, after the sacrificial anode has been degraded by, for example, galvanic corrosion, the remaining portion of implant 110 may start to corrode/degrade. In one embodiment, second material portion 620 and first material portion 610 are combined by plating or welding.

Figure 6:
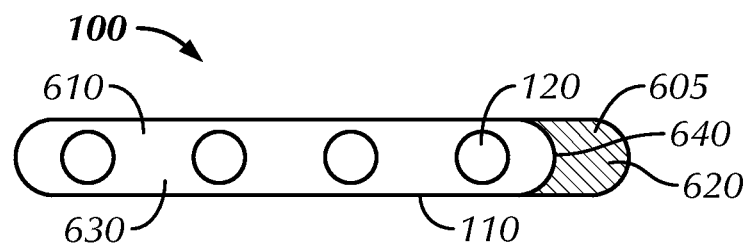
FIG. 6 illustrates an exemplary top view of a tissue implant according to one embodiment of the present invention.

In one embodiment, illustrated in FIG. 6, implant 100 (e.g., a plate) includes a main body 630 having a plurality of apertures 120 at least substantially surrounded by the first material 610 and a prolongation 605 substantially comprising a second material. In one embodiment, prolongation 605 consists essentially of the second material. In one embodiment, prolongation 605 includes second material that is plated over first material. Thus for example, prolongation 605 may include first material portion 610 surrounded by second material portion 620. In one embodiment prolongation 605 is welded to main body 630.

Figure 7:
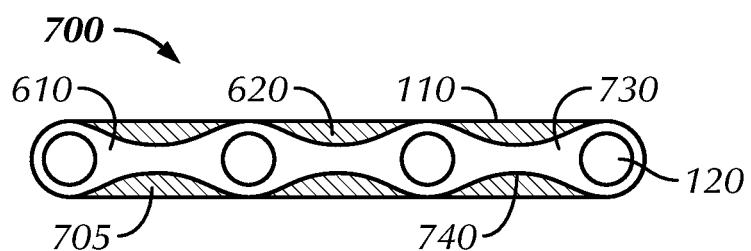
FIG. 7 illustrates an exemplary top view of a tissue implant according to one embodiment of the present invention.

In one embodiment, illustrated in FIG. 7, implant 700 (e.g., a plate) includes a main body 730 having a plurality of apertures 120 at least substantially surrounded by first material 610. Implant 700 may also include segments 705 comprising or consisting essentially of a second material. In one embodiment, main body 730 comprises or consists essentially of first material. In one embodiment, second material is plated over the main body at segments 705.

As illustrated in FIGS. 6 and 7, in some embodiments, implant 100, 700 includes a boundary 640, 740 between first material 610 and of second material 620. In one embodiment, boundary 640 extends from one side of implant 100, 700 to an opposing side of implant 100, 700. In one embodiment, boundary 640 comprises a curved boundary. In one embodiment, boundary 640, 740 forms a scalloped feature as illustrated in FIG. 7. In one embodiment of the present invention, a majority of implant 100, 700 (or a majority of body 110) comprises a first material and a minority of implant 100, 700 comprises a second material and the first and second materials have different degradation characteristics (e.g., nobility). In one embodiment, the second material includes discrete segments relative to the first material.

Figure 9:
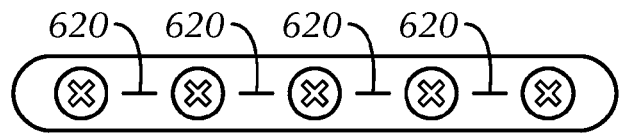
FIGS. 9-11 illustrate exemplary top views of tissue implants according to one embodiment of the present invention.
Figure 10:
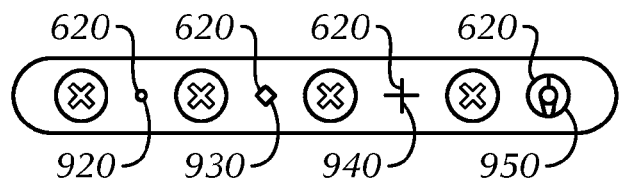

In one embodiment, implant 700 includes a second material that is plated in a pattern over first material. In one embodiment, the second material is electrochemically more noble than the first material. In such an embodiment, the placement of second material may accelerate degradation of implant. In one embodiment, for example, silver may be plated to the top of a degradable iron implant to accelerate the degradation of the iron implant. For example, the pattern of FIG. 7 reflects a multilobated boundary. The pattern of FIG. 9 reflects discrete linear segments of second material 620. The exemplary pattern illustrated in FIG. 10 reflects discrete segments of second material 620 in the form of dots 620, diamonds 930, crosses 940 and logos 950. Discrete segments of other regular or irregular geometric shapes and lines may also be created.

Figure 11:
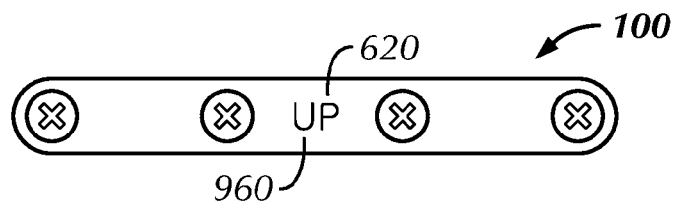

In one embodiment, illustrated in FIG. 11, second material 620 may be configured to provide information 960 to the implanting surgeon. The information for example could provide information 960 regarding the intended placement and/or orientation of implant 100. In one embodiment, information 960 includes material that is more or less noble than the material that makes up the balance of implant 100.

Figure 8:
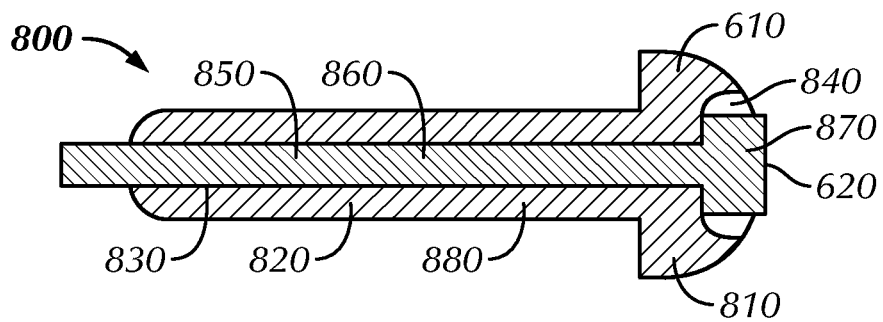
FIG. 8 illustrates an exemplary cross-section view of a tissue implant according to one embodiment of the present invention.

FIG. 8 illustrates an exemplary cross-section view of an implant 800 of the present invention. In one embodiment, implant 800 is a cannulated fastener. Implant 800 may include a main body 880 having a head 810, a shaft 820 (that may or may not be threaded) and a cannula 830 extending through head 810 and shaft 820. Implant 800 may also include a socket 840 that may be contiguous with cannula 820.

In one embodiment, implant 800 also includes an insert 850 that may be configured to fit within cannula 830. In one embodiment, insert 850 is closely fit to cannula 830. In one embodiment, insert 850 includes a shaft 860 and may include a cap 870. In one embodiment, cap 870 is contiguous with shaft 860.

Though FIG. 8 illustrates cap 870 protruding from one end of implant 800 and not filing the entirety of socket 840. Other configurations are within the scope of the present invention. In some embodiment, for example, insert 850 is configured to substantially fill cannula 830 and/or socket 840. In one embodiment, insert 850 is a wire insert that tightly fits within cannula 830. In some embodiments, the cap 870 is "hammered-in" to improve the contact between main body 880 and insert 850.

In one embodiment, the present invention includes a method of controlling the degradation of an implant. In one embodiment, the method includes providing an implant (e.g., an implant that might include a plate or a cannulated screw) having at least one aperture. In one embodiment, the implant of the method has a body that consisting essentially of a first material. The method further includes securing the implant to tissue. In one embodiment, the method includes positioning an insert within the aperture to substantially fill the aperture, the insert consisting essentially of a second material that is of a lower nobility than the first material.

In one embodiment, the method includes providing a first implant (e.g., an implant that might include a plate) having a plurality of apertures and at least one fastener blank. The method might include inserting fasteners through some but not all of the apertures to secure the plate to the bone. After securing the plate to the bone, the method might further include permitting the at least one fastener blank to be inserted in at least one of the plurality of apertures that do not contain an inserted fastener.

Thus, embodiments of the present invention may provide several advantages. For example, in one embodiment, implant 100 may be an implant with a degradation profile that is controlled based upon the materials selected and the designed features of the implant. Thus, whereas a prior art magnesium implant 100 implanted for the purpose, for example, of reducing a fracture, is a bone plate. The plate may include apertures 120 that accommodate bone screws fixing the plate to bone. Prior to the present invention, plate apertures 120 may have been left open in proximity of the fracture. In that instance, plate degradation would be hastened from the interior of the plate to the exterior of the plate as bodily fluids contact the inner face of implant 100 (e.g., the face defining apertures 120). In one embodiment of the present invention, fastener blanks 130 fixed within otherwise open apertures 120 may retard or substantially reduce that degradation. Alternatively, fastener blanks 130 comprising material that is more degradable than the material making up body 110 may be sacrificially degraded in order to further retard the degradation of body 110.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

We claim:

1. An implant system comprising:
   a plate consisting essentially of a first material and having a plurality of apertures;
   a fastener configured to be disposed within at least one of the plurality of apertures and capable of securing the plate to a tissue; and
   a fastener blank configured to be disposed within at least one aperture and to substantially fill the aperture without protruding from the plate, the fastener blank consisting essentially of a second material that is less noble than the first material.

2. The implant system of claim 1, wherein the fastener blank comprises a screw head.

3. The implant system of claim 1, wherein the first material and second material are metallic.

4. The implant system of claim 3, wherein the tissue comprises bone.

5. The implant system of claim 1, wherein the tissue comprises bone.

6. The implant system of claim 1, wherein the fastener blank has a head that is press-fit into the apertures.

7. The implant system of claim 1, wherein the fastener blank has a head that snaps into the apertures.

8. The implant system of claim 1, wherein the fastener blank has a head with no shank.

9. The implant system of claim 1, wherein the fastener blank is a wire.

10. The implant system of claim 1, wherein the fastener blank has a threaded head threaded into the aperture.

11. The implant system of claim 1, wherein the plate and the fastener do not include a coating layer.

12. The implant system of claim 1, wherein the first metallic material is magnesium and the second metallic material is a magnesium alloy.

13. An implant system comprising:
    a plate consisting of a first material and having a plurality of apertures;
    a fastener configured to be disposed within at least one of the plurality of apertures and capable of securing the plate to a tissue; and
    a fastener blank configured to be disposed within at least one aperture and to substantially fill the aperture without protruding from the plate, the fastener blank consisting of a second material that is less noble than the first material.

* * * * *